US00PP32773P2

(12) United States Plant Patent
Berry

(10) Patent No.: US PP32,773 P2
(45) Date of Patent: Jan. 26, 2021

(54) ***HIBISCUS* PLANT NAMED 'JBG AH-21'**

(50) Latin Name: *Hibiscus rosa-sinensis*
Varietal Denomination: JBG AH-21

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 16/602,831

(22) Filed: Dec. 9, 2019

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — The Webb Law Firm

(57) ABSTRACT

A new and distinct *Hibiscus* plant having yellow colored flowers with a dark colored throat and eye zone that last for several days on the plant.

2 Drawing Sheets

Botanical classification: *Hibiscus rosa-sinensis.*
Varietal denomination: 'JBG AH-21'.

BACKGROUND OF THE INVENTION

The present invention comprises a new and distinct *Hibiscus* plant having the varietal name 'JBG AH-21'. The new variety is the result of a planned breeding program with the purposes of developing *Hibiscus rosa-sinensis* plants that exhibit pathogen resistance, multi-day flowers with unique coloration, and possess desirable production traits. 'JBG AH-21' is the result of a cross conducted in Grand Saline, Tex. between *Hibiscus rosa-sinensis* varieties 'JBG 14007' (female parent, U.S. Plant Pat. No. 31,302) and 'JBG 15010' (male parent, unpatented). The new variety was selected in December of 2016 in Grand Saline, Tex. and the first asexual reproduction of the new variety was conducted by semi-hardwood cuttings in February of 2017 in Grand Saline, Tex. 'JBG AH-21' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG AH-21' is similar to both parents in having a yellow toned main flower color with contrasting throat and eye zone colors, as well as having flowers that stay open on the plant for three days. 'JBG AH-21' differs from its female parent in that the new variety exhibits more branching, greater vigor, and darker shades of flower colors. 'JBG AH-21' differs from its male parent in that the new variety has a more mounded plant habit, exhibits better branching, and lacks white colored eye zone extensions.

When 'JBG AH-21' is compared to *Hibiscus rosa-sinensis* variety 'JBG 14002' (U.S. Plant Pat. No. 30,580), both varieties exhibit dark green colored foliage, a high degree of disease resistance, and multi-day, yellow toned flowers with a dark throat color. However, the flowers of 'JBG AH-21' are smaller in size, greater in number, and have petals that are slightly more ruffled around the apex. Further, 'JBG AH-21' exhibits a more mounded growth habit and more branching than 'JBG 14002'.

The following traits distinguish 'JBG AH-21' as a new and distinct cultivar from other *Hibiscus* varieties known to the breeder:

1. Multi-branched, mounded habit, with a high bud count;
2. Yellow colored, textured flowers with a dark throat and bleeding eye zone;
3. High degree of disease resistance, particularly to bacterial leaf spot (*Pseudomonas* spp.);
4. Multi-day flowers; and
5. Dark green colored and glossy foliage.

DESCRIPTION OF THE DRAWINGS

The accompanying photographic images illustrate the new variety at approximately six months of age, with the colors being as nearly true as is possible with color illustrations of this type.

DESCRIPTION OF THE PLANT

Figure 1:
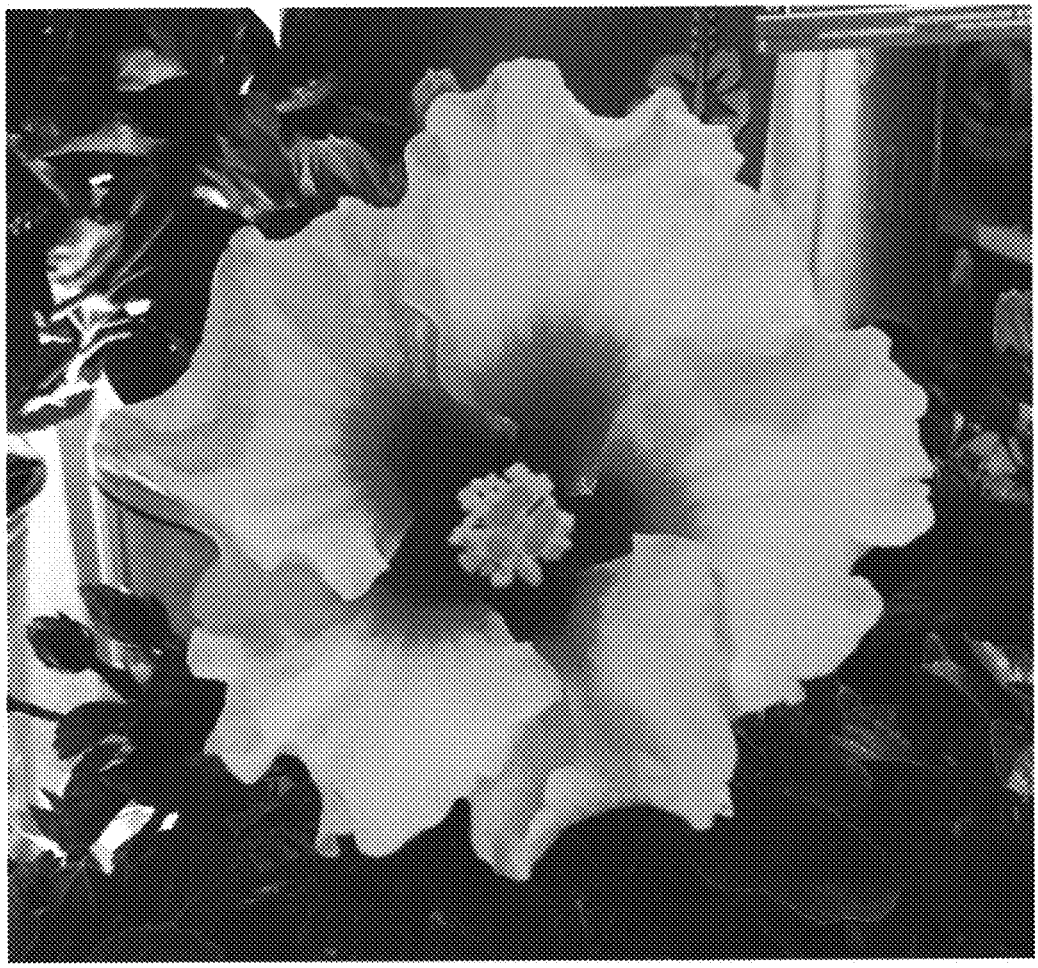
FIG. 1 illustrates a close-up view of a flower of the new variety.
Figure 2:
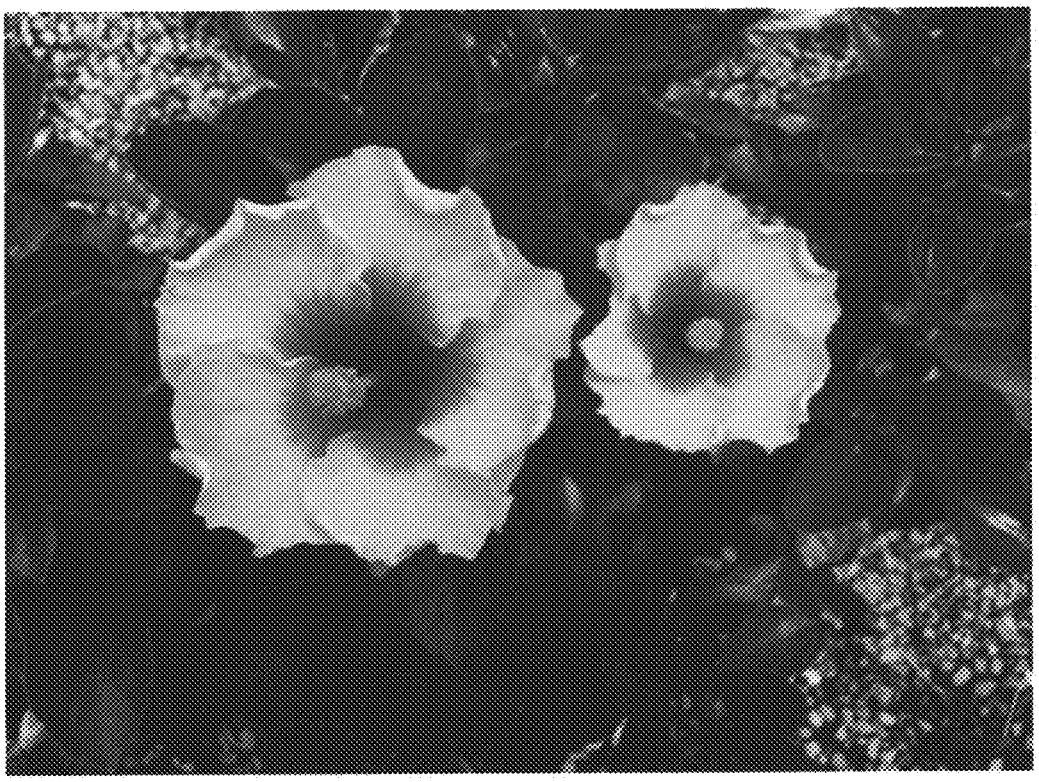
FIG. 2 illustrates a close-up view of two flowers of the new variety.

The following detailed description sets forth the characteristics of the new variety. The plants were grown in a greenhouse heated to a minimum of 16° C. and covered with 33% black shade cloth. The color readings and measurements were taken in the fall in Grand Saline, Tex. under natural light on approximately six months old plants that were grown in 24.0 cm diameter containers. Color references are primarily to The 1995 R.H.S. Colour Chart of The Royal Horticultural Society of London, 3rd Edition, except where general color terms are used.

PLANT

Time to initiate roots: About 45 days at an average of 24° C.

Time to develop roots: About 52 days at an average of 24° C.

Time to produce a finished flowering plant from a rooted cutting: About 32 weeks in a 24.0 cm diameter container.

Specific disease/pest resistance: Resistance to bacterial leaf spot (*Pseudomonas* spp.).

Heat/cold tolerance: Nothing unusual noted to date.

Drought tolerance: Nothing unusual noted to date.

Plant:

*Type*.—Tropical, ornamental shrub.

*Habit*.—Upright; mounded.

*Height*.—75.0 cm.

*Spread*.—70.0 cm.

*Vigor*.—Moderate to strong.

*Rooting*.—Fibrous and well branched.

Stem:

*Number per plant*.—29.

*Length*.—Ranging from 6.0-32.0 cm.

*Width*.—1.5-3.0 mm

*Texture*.—Immature: Smooth, with sparse, short trichomes present. Mature: Vertically ridged.

*Strength*.—Moderate.

*Branch number*.—Approximately 30.

*Internode length*.—1.0-5.0 cm.

*Color*.—Immature: 137C. Mature: 197B.

*Stipules*.—Number per node: 2. Shape: Spinose. Length: 4.0-7.0 mm. Width: 1.0 mm. Surface texture: Smooth, with sparse trichomes present. Apex: Acute. Base: Linear. Margin: Entire. Color: 137C.

Foliage:

*Arrangement*.—Alternate; simple.

*Size of leaf*.—Length: 7.0-9.0 cm. Width: 6.0-7.5 cm.

*Shape of leaf* (*generally*).—Ovate.

*Shape of apex*.—Subacute.

*Shape of base*.—Rounded.

*Texture* (*both surfaces*).—Scabridulous.

*Margin type*.—Crenate.

*Blade lobing*.—Absent.

*Margin variegation*.—Absent.

*Color*.—Young leaves: Upper surface: 137A. Lower surface: 137C. Mature leaves: Upper surface: 137A. Lower surface: 137C.

*Veins*.—Venation type: Pinnate. Color: Upper surface: 137A. Lower surface: 137C.

*Petiole*.—Length: 3.0-4.0 cm. Diameter: 2.0-4.0 mm. Texture: Mostly smooth with a scabrous top surface. Color: 137A generally, but 145A where the petiole joins the leaf base.

FLOWERS

Buds (described two days before flowering):

*Shape*.—Attenuate.

*Diameter*.—2.5 cm.

*Length*.—6.0 cm.

*Color*.—1C generally, with 30B at the apex tip.

Natural flowering season: From spring through fall in Grand Saline, Tex. under outdoor conditions. Semperflorous in a heated greenhouse.

Flower type and habit: Single, with overlapping petals.

Fragrance: None observed.

Flowers:

*Number per stem*.—1.

*Overall depth*.—4.5-6.5 cm.

*Overall diameter*.—9.0-15.0 cm.

*Shape*.—Rotate; regular.

*Lastingness*.—3 days on the plant.

*Petals*.—Number: 5. Arrangement: Simple. Length: 8.0 cm. Width: Apex: 6.5 cm. Base: 1.0 cm. Shape: Ovate. Apex: Obtuse. Base: Acute. Margin: Entire. Texture/appearance: Upper surface: Smooth, with slight ruffling at the apex. Lower surface: Setulose. Color: When opening and fully opened: Upper surface: 13B at the apex through the center and 53A at the throat, with a short (5.0-10.0 mm) eye zone extension of 53C. Lower surface: Generally 13C, with 8D at the base. Attitude: Outermost petals are horizontal.

*Calyx*.—Form: Fused. Overall length: 3.0 cm. Overall diameter: 2.0 cm. Sepals/calyx lobes: Number: 5. Shape: Lanceolate. Apex: Acute. Margin: Entire. Texture: Scabridulous. Color: Outer surface: 143A. Inner surface: 144A.

*Epicalyx*.—Length: 1.7 cm. Width: 5.0 mm. Texture: Scabridulous. Color: 137D.

*Bracts*.—Not present (see epicalyx).

*Peduncle*.—Length: 4.0 cm. Diameter: 3.0 mm. Strength: Strong. Angle: Acute. Texture: Scabridulous. Color: 137D.

Reproductive organs:

*Gynoecium*.—Pistils: Number: 1. Length: 7.5 cm. Stigma: Number: 5. Shape: Round. Length: 3.0 mm. Diameter: 3.0 mm. Color: 25A. Style: Length: 6.0 cm. Width: 3.0 mm at the apex; 5.0 mm at the base. Color: 4D at the apex; 53A at the base. Ovary: Shape: Ovate. Length: 5.0 mm. Width: 4.0 mm. Color: 4D.

*Androecium*.—Stamens: Number: 80. Position: Just below the stigma on the style. Anther: Shape: U-shaped. Diameter: 1.0 mm. Color: 17B. Filament: Length: 5.0 mm. Width: 1.0 mm. Color: 4D. Pollen: Color: 17B. Amount (generally): Moderate.

SEEDS

Seeds:

*Number*.—From 0 to 20.

*Color*.—200C.

*Length*.—4.0 mm.

*Width*.—4.0 mm.

I claim:

1. A new and distinct variety of *Hibiscus* plant, as is herein illustrated and described.

* * * * *